United States Patent [19]

Young et al.

[11] Patent Number: 5,179,001

[45] Date of Patent: Jan. 12, 1993

[54] DETECTION AND MONITORING OF CHRONIC AND GRAM-NEGATIVE INFECTION

[75] Inventors: Lowell S. Young, San Francisco; Mark A. Jacobson, Oakland, both of Calif.

[73] Assignee: The Regents of the University of California, Oakland, Calif.

[21] Appl. No.: 581,432

[22] Filed: Sep. 12, 1990

Related U.S. Application Data

[63] Continuation of Ser. No. 912,439, Sep. 26, 1986, abandoned, which is a continuation-in-part of Ser. No. 855,878, Apr. 24, 1986, abandoned, which is a continuation-in-part of Ser. No. 781,242, Sep. 27, 1985, abandoned.

[51] Int. Cl.⁵ .................. G01N 23/569; G01N 33/53; G01N 23/53
[52] U.S. Cl. .................... 435/732; 435/792; 436/529
[58] Field of Search .............. 436/548, 529; 435/7.2, 435/7.32, 7.92

[56] References Cited

U.S. PATENT DOCUMENTS

| | | | |
|---|---|---|---|
| 4,079,126 | 3/1978 | Homme et al. ................ | 435/878 |
| 4,587,121 | 5/1986 | Collins . | |
| 4,596,769 | 6/1986 | Shockman et al. . | |
| 4,652,518 | 3/1987 | Makela et al. . | |
| 4,683,196 | 7/1987 | McLaughlin . | |
| 4,702,910 | 10/1987 | Fukuda et al. ................ | 530/350 |
| 4,707,543 | 11/1987 | Zollinger et al. ............ | 435/875 |
| 4,777,136 | 10/1988 | Young ......................... | 435/240.27 |

FOREIGN PATENT DOCUMENTS

| | | |
|---|---|---|
| 0163493 | 12/1985 | European Pat. Off. . |
| 0174204 | 3/1986 | European Pat. Off. . |
| 0183876 | 6/1986 | European Pat. Off. . |
| WO84/04458 | 11/1984 | PCT Int'l Appl. . |
| WO85/01659 | 4/1985 | PCT Int'l Appl. . |

OTHER PUBLICATIONS

Engels, W. et al., Inf. Immun., 49:182–189, Jul. 1985.
Hancock, R. E., et al., Inf. Immun., 42:170–177, Oct. 1983.
Angarano, G. et al., J. Clin. Micro, Jun. 1984: 905–910.
Rowe and Meadow, Eur. J. Biochem. (1983) 132:329–37.
Meadow, et al. J. Gen. Microbio. (1984) 130:631–44.
Appelmelk et al., J. Immuno. Meth. 91985) 82:199–207.
Gascon et al., 25th ICAAC, Minneapolis, Minn. (1985) Abstract No. 77.
Poxton et al., FEMS Microbiology Letter (1985) 27:247–51.
Wilmott et al., AJDC (1985) 139:669–671.
Young et al., "Core Glycolipid . . . ," Proc. Soc. Exp. Biol. & Med., 149:389–396 (1975).
Young et al., "Cross-Protective Immunity . . . ," J. Infect. Dis., 136:SA174–S180 (1977).
Hiernaux et al., "Study of the Idiotypy of Lipopolysaccharide-Specific Polyclonal and Monoclonal Antibodies," Eur. J. Immunol., 12:797–803 (1982).
Mutharia et al., "Surface Localization of Pseudomonas aeruginosa Outer Membrane Porin Protein F by Using Monoclonal Antibodies," Infect. and Immun., 42:1027–1033 (Dec. 1983).
Pollack et al., "Enhanced Survival in Pseudomonas aeruginosa Septicemia Assocated with High Levels of Circulating Antibody to Escherichia coli Endotoxin Care," J. Clin. Invest., 72:1874–1881 (1983).

(List continued on next page.)

Primary Examiner—John Doll
Assistant Examiner—Susan L. Futrovsky
Attorney, Agent, or Firm—Townsend and Townsend

[57] ABSTRACT

The present invention provides novel compositions and methods useful in the diagnosis and monitoring of Gram-negative infection, especially chronic Pseudomonas aeruginosa infection associated with cystic fibrosis. Pseudomonas aeruginosa strain PAC 605 core lipopolysaccharide determinants are employed as a solid phase antigen in enzyme linked immunosorbant assays and Western blot immunoassay to measure human IgG response to P. aeruginosa infection. The novel compositions are provided in kit form for use in assay methods according to the present invention.

5 Claims, 2 Drawing Sheets

OTHER PUBLICATIONS

Darveau, R. P. and Hancock, R. E. W., "Procedure for Isolation of Bacterial Lipopolysaccharides from both Smooth and Rough *Pseudomonas aeruginosa* and *Salmonella typhimuium* strains," *J. Bacteriol.*, 155:831–838 (1983).

Sawada et al., "Protection Against Infection with *Pseudomonas aeruginosa* by Passive Transfer of Monoclonal Antibodies to Lipopolysaccharides and Outer Membrane Proteins," *J. Infect. Dis.*, 150:570–576 (1984).

Young et al., *Clin. Res.* 32:518A (1984).

Mutharia et al., "Monoclonal Antibodies Specific for *Escherichia coli* J5 Lipopolysaccharide: Cross-Reaction with Other Gram-Negative Bacterial Species," *Infect. Immun.*, 45:631–636 (Sep. 1984).

Dunn et al., "Enhanced Survival During Murine Gram-Negative Bacterial Sepsis by Use of a Murine Monoclonal Antibody," *Arch. Surg.*, 120:50–53 (1985).

Dunn et al., "Efficacy of Type-Specific and Cross--Reactive Murine Monoclonal Antibodies Directed Against Endotoxin During Experimental Sepsis," *Surgery*, 98:283–290 (Aug. 1985).

Hancock et al., "Monoclonal Antibodies Against Bacterial Outer Membrane Antigens," *Adv. Exp. Med. and Biol.*, 185:215–222 (1985).

MacDonald, A. B., "Antigens of *Chlamydia trachomatis*," *Rev. Infect. Dis.*, 7:731–736 (1985).

Sawada et al., "Characterization of a Human Monoclonal Antibody to Lipopolysaccharides of *Pseudomonas aeruginosa* Serotype 5: A Possible Candidate as an Immunotherapeutic Agent for Infections with *P. aeruginosa*," *J. of Infec. Dis.*, 152:965–970 (Nov. 1985).

Sawada et al., "A New Common Polysaccharide Antigen of Strains of *Pseudomonas aeruginosa* Detected with a Monoclonal Antibody," *J. Infect. Dis.*, 152:1290–1299 (1985).

Mackie et al., "Immune Respone of the Mouse to Gram-Negative Bacterial Outer Membrane Extracts as Assessed with Monoclonal Antibodies," *The J. of Immunology*, vol. 129, No. 2, pp. 829–832 (Aug. 1982).

Nelles et al., "Mouse Monoclonal Antibodies Reactive with J5 Lipopolysaccharide Exhibit Extensive Serological Cross-Reactivity with a Variety of Gram-Negative Bacteria," *Infec. and Immun.*, vol. 46, No. 3, pp. 677–681 (Dec. 1984).

Gigliotti et al., "Failure of Monoclonal Antibodies to Core Glycolipid to Bind Intact Smooth Strains of *Escherichia coli*," *J. of Infec. Dis.*, pp. 1005–1011, vol. 151, No. 6 (Jun. 1985).

Peters et al., "Monoclonal Antibodies to Enterobacterial Common Antigen and to *Escherichia coli* Lipopolysaccharide Outer Core: Demonstration of an Antigenic Determinant Shared by Enterobacterial Common Antigen and *E. coli* K5 Capsular Polysaccharide," *Infection and Immunity*, vol. 50, No. 2, pp. 459–466 (Nov. 1985).

Teng et al., "Protection against Gram-negative bacteremia and endotoxemia with human monoclonal IgM antibodies," *Proc. Natl. Acad. Sci. U.S.A.*, vol. 82, pp. 1790–1974, (Mar. 1985).

Campbell, Ailsa M., "Monocolonal Antibody Technology The Production and Characterization of Rodent and Human Hybridomas," *Laboratory Techniques in Biochemistry and Molecular Biology*, vol. 13, pp. 86–101 (1984).

Sudo et al., *Chem. Abstr.*, 104:147,025m (1986).

Fukuda et al., *Chem. Abstr.*, 104:147,026n (1986).

Mutharia et al., *Chem. Abstr.*, 100:33069r (1984).

Sawada et al., *Chem. Abstr.*, 101:22826b (1984).

DETECTION AND MONITORING OF CHRONIC AND GRAM-NEGATIVE INFECTION

CROSS REFERENCE TO RELATED APPLICATION

This is a continuation of application Ser. No. 06/912,439, filed Sep. 26, 1989, now abandoned which application is a continuation-in-part of U.S. application Ser. No. 8,55,878, filed Apr. 24, 1986, now abandoned, the disclosures of which are hereby incorporated by reference, which is a continuation-in-part of U.S. application Ser. No. 781,242, filed Sept. 27, 1985, now abandoned.

BACKGROUND OF THE INVENTION

1. Field of the Invention

The present invention relates generally to infectious diseases and, more particularly, to the diagnosis of chronic *Pseudomonas aeruginosa* infection especially as associated with cystic fibrosis.

Cystic fibrosis (CF) is the most common lethal genetic syndrome among Caucasians. In the United States, the incidence is 1 in 2,000 live births. CF is a generalized metabolic disorder involving change in the serous and mucous secretions resulting in, among other symptoms, progressive obstructive pulmonary disease and malabsorption due to pancreatic enzyme insufficiency. As late as the 1950's, life expectancy for cystic fibrosis patients was extremely short. Even today, only half of CF patients reach their 20th birthday.

Pulmonary complications associated with progressive obstructive pulmonary disease are responsible for the majority of morbidity and virtually all mortality in afflicted patients. Pulmonary infections are generally a fact of life for the CF patient. The majority of these infections are caused by the gram-negative bacterium *Pseudomonas aeruginosa* (PA). Once established in CF patients, PA is an extremely difficult organism to eradicate. The majority of CF patients are chronically infected with PA.

Treatment of chronic PA infection with antibiotics, including the aminoglycosides, generally fails to eradicate PA. Indeed, some researchers believe that the continuous use of antibiotics actually contributes to the bacteria's persistence. It is not uncommon to find patients infected with PA strains resistant to all known antibiotics. These patients often have an unrelenting deterioration of pulmonary function ultimately leading to death. A recent study reported survival rates to age 16 years in CF afflicted children with and without chronic PA infection. The researchers reported a 53% survival rate in infected children versus an 84% survival rate in non-infected children.

Recent advances in the treatment of gram-negative bacterial infections, particularly PA infections, provide hope for CF patients with chronic PA infections. Methods employing monoclonal antibody compositions, such as those disclosed in U.S. patent application Ser. No. 855,878, appear particularly promising. Before any therapy can be effective, however it is important to accurately diagnose the nature of the infection. Once diagnosed, it is extremely beneficial to follow the effectiveness of therapy throughout its course. There is therefore a need for compositions and methods useful in the diagnosis of chronic PA infection and in following the course of such infection.

2. Discussion of the Relevant Literature

U.S. Pat. No. 4,587,121 discloses the use of hyperimmune serum globulin having high titers of antibody against all seven Fisher Immunotypes of *Pseudomonas aeruginosa* for use in treating patients with Pseudomonas infection.

Rowe and Meadow, *Eur. J. Biochem.* (1983) 132:329–37, report the isolation of lipopolysaccharides from *Pseudomonas aeruginosa* strain PAC1R and its lipopolysaccharide-defective mutants.

Meadow et al., *J. Gen. Microbio.* (1984) 130:631–44, describe the characterization of surface antigens in *Pseudomonas aeruginosa*.

Appelmelk et al., *J. Immuno. Meth.* (1985) 82:199–207, describe an enzyme linked immunosorbant assay (ELISA) for the measurement of antibodies to different parts of gram-negative lipopolysaccharide core region employing core antigens of *E. coli* J5 LPS, *Salmonella minnesota* R595 LPS or *E. coli* lipid A.

Gascon et al., 25th ICAAC, Minneapolis, Minn., (1985) Abstract No. 77, describe the functional activity of monoclonal antibodies against common core lipopolysaccharide antigen of *P. aeruginosa*.

Poxton et al., *FEMS Microbiology Letter* (1985) 27:247–51, describe the association on SDS-polyacrylamide gels of lipopolysaccharide and outer membrane proteins of *P. aeruginosa* as revealed by monoclonal antibodies and Western blotting employing *P. aeruginosa* Habs serotypes 1 and 4.

Wilmott et al., *AJDC* (1985) 139:669–71 report cystic fibrosis survival rates and the influences of allergy and *Pseudomonas aeruginosa*.

SUMMARY OF THE INVENTION

The present invention provides novel compositions and methods useful in the diagnosis and monitoring of Gram-negative infection, especially chronic *Pseudomonas aeruginosa* infection associated with cystic fibrosis. *Pseudomonas aeruginosa* strain PAC 605 core lipopolysaccharide determinants are employed as a solid phase antigen in enzyme linked immunosorbant assays and Western blot immunoassay to measure human IgG response to *P. aeruginosa* infection. The novel compositions are provided in kit form for use in assay methods according to the present invention.

BRIEF DESCRIPTION OF THE FIGURES

FIG. 3 is an immunoblot analysis of patient sera vs. proteinase K digestion and periodate oxidation of PAC 605 LPS: and FIG. 4 is an immunoblot analysis of patient sera vs. J5 *E. coli* LPS.

DETAILED DESCRIPTION OF THE PREFERRED EMBODIMENTS

Figure 1:
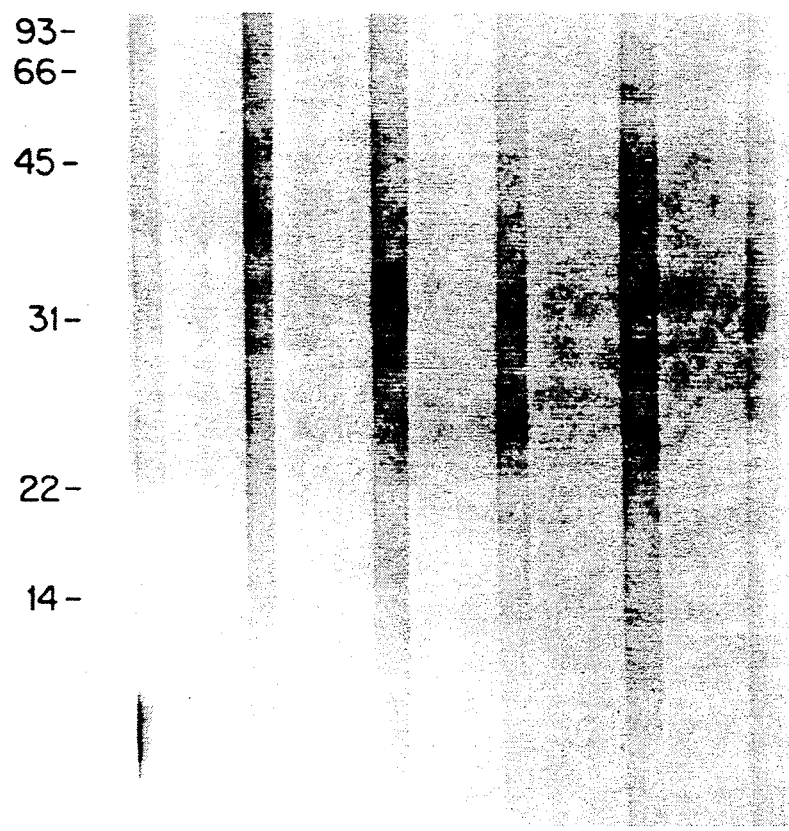
FIG. 1 is an immunoblot analysis of patient sera.

The present invention provides those skilled in the art with novel compositions and methods for the diagnosis and monitoring of chronic gram-negative infections, particularly *Pseudomonas aeruginosa* infection associated with cystic fibrosis. The subject compositions comprise core lipopolysaccharide derived from *Pseudomonas aeruginosa* strain PAC 605, especially antigenic determinants found on such core lipopolysaccharide. The compositions are employed in diagnostic methodology such as enzyme linked immunosorbant assay (ELISA) and Western blot assay.

According to the present invention, the novel compositions are employed because of their ability to bind immunoglobulin molecules (antibodies or active fragments thereof) which bind antigenic determinants on gram-negative bacteria. Donors of particular interest include human patients afflicted with cystic fibrosis. Immunoglobulin molecules of particular interest include human IgG molecules.

According to the method of the present invention, the novel antigenic determinant compositions are bound to a solid support and employed in a variety of assay techniques well-known to the art, particularly ELISA. Western blot analysis, or the like. Solid supports of particular interest include a particle, e.g., bead, fiber, or the like, or container wall and include materials such as nitrocellulose, cellulose, agarose, polystyrene, dextran, glass, polymer coated magnetic metals, nylon, silica gel, polyacrylamide, polymethyl, methacrylate, and the like, and of particular interest is nitrocellulose (NC).

The composition may be coupled directly to the support or via a spacer arm to aid in preventing any possible charge or steric interferences with antigen binding. Various spacer arms are available and well known in the art. The ratio of antibody to support may be about 100:1 usually about 1,000:1 or higher.

According to the present invention, kits are provided comprising lipopolysaccharide derived from *Pseudomonas aeruginosa* strain PAC 605 cells. These compositions may be provided in kit form bound to a solid support and may include reagents employed in any of a variety of assay techniques well known to those skilled in the art. These kits find particular utility in diagnosing and monitoring chronic *Pseudomonas aeruginosa* infection in cystic fibrosis patients.

The following examples are offered by way of illustration and not limitation.

Experimental

EXAMPLE I—MATERIALS AND METHODS

1. LPS: PAC 605 bacterial strain (parent strain PAC1R, Habs 0:3) was deposited on Sep. 27, 1985 with the American Type Culture Collection (A.T.C.C.). Rockville, Md., Accession No. 53273. Cells were grown in a aerated fermenter and LPS was extracted using the method described by Darveau and Hancock, *J. Bacteriology* (1983) 155:831–38, which is incorporated by reference. Coomasie blue dye protein assay (BIORAD) measured a protein contamination of 1%. Purified J5 *E. coli*, Fisher type 1 PA, and *Salmonella minnesota* Ra LPS were purchased from LIST Biological Laboratories.

2. Anti-PA core LPS monoclonal antibody: XMMPS-605 (A.T.C.C. Accession No. HB8909 is an IgG2b murine monoclonal antibody (MoAb). It was produced by fusing spleen cells with SP2/0 myeloma cells following immunization with killed PAC 605 cells. Hybrids were screened by using purified PAC 605 as antigen. XXMPS-605 -is cross-reactive, binding to the core region of LPS from all 7 Fisher types of PA.

3. Patient sera: Normal human sera was donated by laboratory workers with no history of PA infection or of working with PA organisms. Patient sera was made available by the clinical laboratories of UCLA Center for the Health Sciences, Los Angeles, Calif., and Pacific Medical Center, San Francisco, Calif. Samples used were from excess serum obtained for routine chemistry and antibiotic levels.

4. IgG ELISA: An ELISA was developed and standardized to measure human IgG titer against purified PAC 605 LPS.

a) 25 $\mu$l of PAC 605 LPS (500 $\mu$/ml in distilled water with 0.05% triethylamine (TEA), boiled for 2 hours before use) and 25 $\mu$l of 0.02M $MgCl_2$ with 0.05% TEA were added to triplicate wells of polystyrene COSTAR 96-well EIA plates which were then covered and incubated overnight at 37° C.

b) Wells were washed three times with phosphate-buffered saline (PBS) with 0.02M $MgC_2$, pH 7.1. 100 $\mu$l of 1% gelatin in PBS/$MgCl_2$ was then added to LPS coated wells and triplicate control wells and incubated overnight at room temperature.

c) The next day 50 $\mu$l of human serum diluted serially in 0.1% gelatin in PBS/$MgCl_2$ was added to triplicate LPS coated and control wells and incubated for one hour. All plates had positive test controls (XMMPS-605 20 $\mu$g/ml) and negative test controls (pooled human serum from 4 volunteers, mixed just before use and diluted 1/640) added to triplicate LPS coated and control wells.

d) All wells were washed three times, then 50 $\mu$l of Protein A-peroxidase (BIORAD) diluted 1/10,000 in 0.1% gelatin in PBS/$MgCl_2$ was added to all wells and incubated for one hour.

e) Wells were washed 5 times, then 100 $\mu$l aliquots of ABTS substrate was added to each well (per 5 ml: 4.9 ml 0.1M disodium citrate buffer, pH 4.5; 0.1 ml of 2.2′-azino-d-[3-ethyl-benzthiazolinesulfonate {6}] (BOEHRINGER MANNHEIM), 20 mg/ml in citrate buffer; 5 $\mu$l 30% $H_2O_2$.

f) Optical density (O.D.) was read on an automated microreader (BIOTEK or FLOW LABORATORIES) when the O.D. of the positive plate control (XMMPS-605) was close to 1.0. Results of triplicate test and control O.D.'s were averaged. For a given test sample dilution, the mean control O.D, was subtracted from the mean test O.D. A positive serum titer was defined as that dilution yielding an O.D. greater than that of pooled human sera diluted 1/640 (negative control) recorded on the same plate.

5. Serum IgG levels: Patient and volunteer serum IgG levels were determined by radial immunodiffusion, using KALLESTAD IgG Endoplates. KALLESTAD low, medium, and high reference sera were used as controls.

6. SDS-polyacrylamide gel electrophoresis: PAC 605 and J5 *E. coli* purified LPS were fractionated on SDS-polyacrylamide slab gels with a discontinuous buffer system as described by Hames, B. D., *Gel electrophoresis of Proteins: A Practical Approach*, (1981) IRL Press, Oxford, England, P. 1–93. The separating gel contained 12.5% acrylamide/methylene bisacrylamide (30.0/0.8) in Tris/SDS buffer, pH 8.8. The stacking gel contained 4.5% acrylamide/methylene bisacrylamide in Tris/SDS buffer, pH 6.8. 350 $\mu$g of LPS was boiled for 10 minutes in final sample buffer and applied to a sample well. A lower molecular weight standard was applied to a control well. Gels were electrophoresed at 8 mAmps overnight, then at 18 mAmps until the tracking dye reached the bottom.

7. Electrophoretic transfer and immunoblot: Gels were immediately transferred to nitrocellulose for three hours at constant amperage (190 mAmp) using the Western blot method of Towbin et al., *Proc. Nat. Acad. Sci. USA* (1979) 76:4350–54. Molecular weight lanes were cut and stained with amide black in acetic acid and methanol. The remainder of the sheet was allowed to dry then stored at −20 degrees Centigrade until use. For immunoassay of these blots, 0.5 cm strips were cut and blocked for 30 minutes in 1% gelatin in PBS. Individual strips were then incubated on a rocker overnight with 4 ml of a 1/40 dilution of human serum in 0.1% gelatin in PBS. Positive control strips for each blot were incubated with either XMMPS-605, 20 μ/ml, or rabbit anti-J5 E. coli serum, 1/40 dilution. The following day strips were washed for one hour with 4 changes of PBS, then incubated in a 1/2000 dilution of Protein A-peroxidase, then washed for one hour with 6 changes of PBS. Strips were developed with 4 chloro-1-naphthol substrate (per 5 ml: 4 ml PBS, 1 ml of 0.3% w/v 4 chloro-1-naphthol [SIGMA] in reagent grade methanol, 5 μl 30% $H_2O_2$). When optimal color change had occurred. NC strips were washed in water.

8. Proteinase K digestion and periodate oxidation of LPS: To confirm that bands seen on immunoblots of LPS represent non-protein, carbohydrate determinants, 175 μg of PAC 605 LPS was pre-digested with Proteinase K (BRL) 1 mg/ml frozen stock added in a 1:10 v/v ratio to LPS in final sample buffer and incubated overnight at 55 degrees Centigrade. An additional aliquot of Proteinase K was added the next day and incubated for three more hours. This digested LPS was fractionated in one half of an SDS-polyacrylamide gel while an equal amount of undigested PAC 605 LPS was fractionated on the other half. SDS-PAGE and Western blot were performed as previously described. Strips containing digested and non-digested LPS were immunoblotted with positive patient sera.

Additional strips of blotted proteinase-treated PAC 605 LPS were oxidized with periodic acid to destroy carbohydrate epitopes, then immunoassayed using the same positive patient sera. Western blot strips of PAC 605 LPS and control immunodots of Salmonella minnesota Ra LPS were blocked in 1% gelatin in PBS, then bathed overnight at 4 degrees Centigrade in 50 mM periodic acid, 50 mM acetic acid, pH5. After brief washing, strips and control immunodots were immunoassayed as previously described. An IgG2a MoAb specifically reactive with Salmonella Ra LPS was strongly reactive against the control Ra immunodot but completely unreactive against the periodate-oxidized Ra LPS dot.

9. Silver stain: To confirm location of LPS bands, SDS-PAGE was done with individual lanes containing PAC 605 LPS. J5 E. coli LPS and several other PA LPS controls. This gel was then silver stained using the method described by Hitchcock and Brown, J. Bacteriology (1983) 154:269-77, which is incorporated by reference.

EXAMPLE II—RESULTS

1. IgG ELISA: Results of the ELISA used to detect human IgG antibodies to PAC 605 LPS are summarized in Tables 1, 2, and 3.

Convalescent sera were available for 10 patients with documented PA bacteremia. Five of these patients had documented localized infection prior to the onset of bacteremia (pneumonia [2], brain abscess [1], cystitis [1], sinusitis [1]). The geometric mean titer of these 10 patients (obtained a minimum of seven days after blood cultures were drawn) was 1/171 (range 1/40-1/1280). This did not differ significantly from the geometric mean titer of sera from 5 normal volunteers (mean 1/211, range 1/160-1/320, p>0.5, Student's test) or of convalescent sera of 11 patients with documented non-PA enteric gram-negative bacteremia (mean 1/97, range 1/40-1/320. p>0.5). Blood culture isolates from this latter group included E. coli (3), Klebsiella pneumonia (3), Enterobacter cloacae (3), Proteus mirabilis (2), and Aeromonas hydrophila (1).

TABLE 1

Geometric Mean IgG anti-PAC LPS Titers

| | Number of patients | Mean titer | Range | P value* |
|---|---|---|---|---|
| PA bacteremia, convalescent | 10 | 1/171 | 1/40-1/1280 | p > 0.5 |
| Non-PA gram-negative bacteremia, convalescent | 11 | 1/97 | 1/40-1/320 | p > 0.5 |
| Cystic fibrosis | 18 | 1/1808 | 1/320-1/10,000 | p < 0.001 |
| Normal volunteers | 5 | 1/211 | 1/160-1/320 | p > 0.5 |

*Student's t test

TABLE 2

Paired Acute and Convalescent Mean IgG Anti-PAC 605 LPS Titers

| | Number of Patients | Acute | Convalescent | P value* |
|---|---|---|---|---|
| PA bacteremia | 6 | 1/143 | 1/160 | p > 0.5 |
| Non-PA gram-negative bacteremia | 11 | 1/132 | 1/97 | p > 0.5 |

*Student's t test

Paired acute and convalescent sera were available from 6 patients with PA bacteremia and all 11 patients with non-PA gram-negative bacteremia. Geometric mean acute and convalescent IgG titers did not significantly differ in either group. PA bacteremic patients had a mean acute titer of 1/143 (range 1/20-1/1280) and convalescent titer of 1/160 range 1/40-1/1280, p>0.5). As mentioned above, 5 of the PA bacteremic patients had documented recent localized PA infection. Acute and convalescent titers were available for 4 of these 5 patients (Table 3). Three of these patients showed no increase in IgG anti-PAC 605 LPS titer, while one demonstrated a four-fold rise between acute and convalescent sera.

TABLE 3

Individual Acute and Convalescent IgG Anti-PAC 605 LPS Titers of PA Bacteremic Patients with Documented Prior, Localized PA Infection

| Source of prior localized infection | Acute titer | Convalescent* titer |
|---|---|---|
| Pneumonia | 1/160 | 1/80 |
| Pneumonia | 1/320 | 1/1280 |
| Sinusitis | 1/40 | 1/40 |
| Brain abscess | 1/160 | 1/160 |

*obtained at least 7 days after initial blood culture drawn

Random serum was also available from 18 patients with cystic fibrosis (CF) and chronic PA pulmonary infection. The geometric mean titer of these patients was significantly higher (mean 1/1808, range 1/320-1/10,000) than the mean titer of normal volunteers (p<0.001) and the mean convalescent titer of patients with PA (p<0.001) bacteremia.

IgG Levels: Hypogammaglobulinemia was excluded as the reason for the surprisingly low IgG anti-PAC 605 titer observed in convalescent sera of PA bacteremic patients compared to uninfected normal volunteers. Serum IgG levels were measured and compared. The mean IgG level of the 10 PA bacteremic patients (1.118 mg/dl, range 640-1680 mg/dl) did not differ significantly from the mean of 5 normal volunteers (1.236 mg/dl, range 1000-1380 mg/dl, p>0.5). The CF patients' markedly higher IgG titer to PAC 605 LPS could have been a nonspecific artifact related to higher IgG levels. To test this hypothesis, 9 of the 18 CF patients' sera were randomly chosen and IgG levels were measured. The mean IgG level of these 9 patients was 1734 mg/dl, compared to 1118 mg/dl in the 10 PA bacteremic patients—not a significant difference (p>0.1).

3. Western blots of PAC 605 LPS: In order to reveal the exact nature of the PAC 605 LPS determinants bound by human IgG, whole SDS-polyacrylamide gels were loaded with LPS, then fractionated by electrophoresis, then transferred by the Western blot method to nitrocellulose (NC) sheets. These sheets were cut into strips, incubated first with 1/40 patient sera, then with Protein A-peroxidase and finally developed with substrate. All data was confirmed by incubating the same test sera with a second strip blotted from a different prep gel of PAC 605 LPS. Results are summarized in Table 4. Several distinct band patterns were seen, and examples of each pattern are shown in FIG. 1. As a positive control for each prep gel that was blotted, the murine monoclonal IgG2a designated XMMPS-605 (which is sensitive and specific for the core determinants of PAC 605 LPS) was reacted with one NC strip. This reproducibly showed an intense broad band between 10 kD and the dye front (see FIG. 1, lane A). No bands were visible when pooled normal human sera or convalescent sera of patients with PA bacteremia were incubated with strips of fractionated, blotted PAC 605 LPS. However 13 of 18 CF patients showed one of the following three patterns. Five patients demonstrated a single broad core band between 10 kD and the dye front (same pattern as that shown by the anti-PA core LPS monoclonal antibody XMMPS-605). Three patients showed a faint typical smooth LPS ladder pattern between 30 and 50 kD. Five patients showed both core and 30-50 kD ladder bands. One additional patient (RR) had a broad core band in combination with two narrow intense bands at 14 kD and 24 kD. When this immunoblot was repeated using PAC 605 LPS pretreated with Proteinase K before electrophoresis, the 14 kD band disappeared suggesting it represented a protein determinant. Only 4 of the 18 had a low molecular weight core band and 8 of 18 had faint higher molecular weight ladder bands.

TABLE 4

| PAC 605 LPS | Western Blot Band Patterns of PAC 605 LPS and J5 E. coli LPS | | |
|---|---|---|---|
| | Cystic fibrosis patient sera | PA bacteremic convalescent sera | P value* |
| Broad band <10 kD | 11/18 | 0/10 | p < 0.01 |
| Ladder bands, 30-50 kD | 8/18 | 0/10 | p < 0.05 |
| J5 E. coli LPS Broad band <10 kD | 11/17 | 3/9 | p > 0.1 |

*Chi square with Yate's modification

Figure 2:
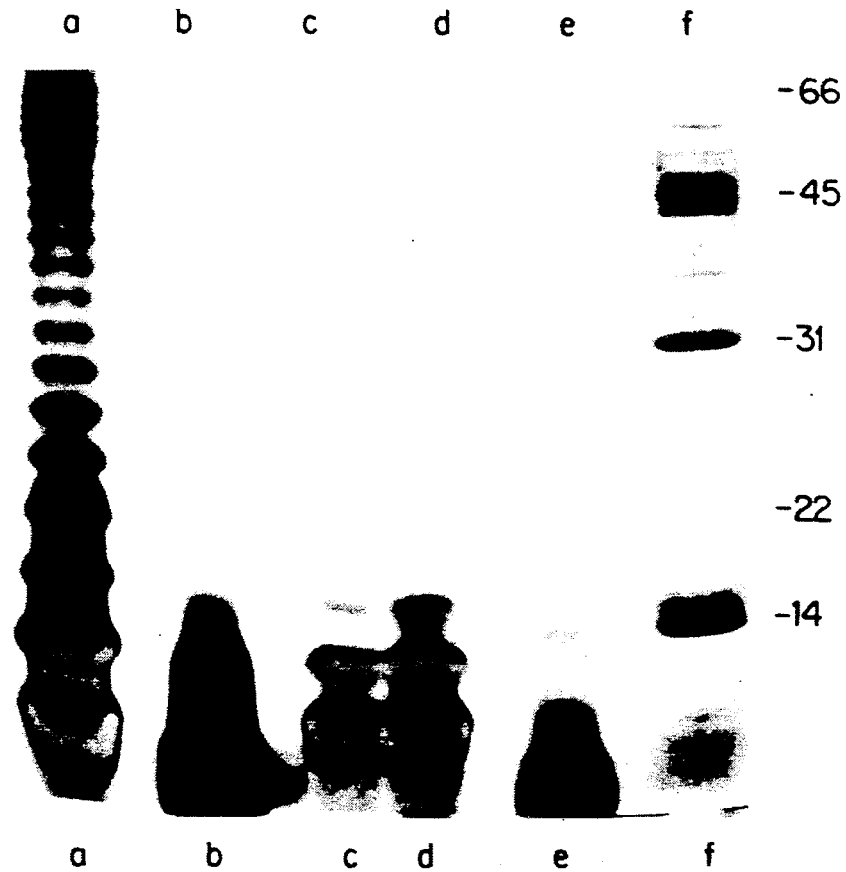
FIG. 2 is a silver stain of SDS-PAGE.

4. Silver stain of PAC 605 LPS: The appearance of 30-50 kD ladder bands was unexpected since PAC 605 LPS does not have smooth LPS. Several studies were done to elucidate the nature of these bands. PAC 605 LPS and several control purified LPS samples were fractionated by SDS-PAGE, then silver-stained to exclude the possibility of contamination. Twenty-five µg of PAC 605 LPS run in a single lane (FIG. 2, lane E) showed an intense core band from 10 kD to the dye front—the exact location of the broad core band seen on Western blots reacted with both the anti-core MoAb XXMPS-605 and with 11 of the 18 CF patient sera. There were narrow sharp bands at 14 kD and 24 kD corresponding to the bands that occurred with CF patient RR's sera. The band at 14 kD may represent a protein-LPS complex since this band disappeared from RR's immunoblot when PAC 605 was pre-treated with Proteinase K. No bands were seen between 30 and 50 kD—the location of faint ladder bands on Western blot strips. As a control, Proteinase K digested boiled whole cells of a rough, non-typable sputum PA isolate from one of the CF patients were fractionated in the same gel (FIG. 2, lanes C and D). This apparently rough isolate has small amounts of high molecular weight smooth LPS faintly detectable when $7.5 \times 10^8$ cells were run in lane C, and clearly visible when $1.5 \times 10^9$ cells were run in lane D. Another gel run by SDS-PAGE was loaded with 25-125 µg of PAC 605 LPS per well. Silver stain of the overloaded wells showed a diffuse smear throughout the lane. Individual ladder bands, however, were not visible.

5. Proteinase K digestion and periodate oxidation of PAC 605 LPS: Immunoblots were repeated to determine the exact nature of these high molecular weight ladder bands. First PAC 605 LPS was pre-digested with Proteinase K to destroy any protein determinants before fractionating by SDS-PAGE and immunoblotting. NC strips of blotted, Proteinase K-digested LPS and untreated LPS were reacted with two CF patient s sera that had previously shown ladder bands (FIG. 3, lanes A and C). Ladder bands remained visible after Proteinase K treatment, suggesting the bands are not due to protein epitopes. Several of these LPS strips were then oxidized overnight with periodic acid, pH 5, to destroy carbohydrate determinants, as described by Caldwell and Hitchcock, Infect. Immun. (1984) 44:306-14, which is incorporated by reference, and then reacted with the same CF patient's serum. Ladder bands disappeared after periodate oxidation, suggesting that the responsible determinants are located on repeating polysaccharide units of smooth LPS.

6. Western blots of J5 E. coli LPS: If the core determinants of PAC 605 LPS are very similar to those of the cross-reactive core of enteric gram-negative bacilli (i.e. purified J5 E. coli LPS), then the difference in IgG anti-PA core LPS response between CF and convalescent PA bacteremic patients may just be a reflection of a difference in cross-reactive IgG anti-gram-negative core titer. To test this hypothesis, J5 E. coli LPS was fractionated by SDS-PAGE and Western blotted onto NC sheets. Individual NC strips were immunoassayed with sera from 17 CF patients and 9 convalescent PA bacteremic patients. All results were confirmed by incubating the same test serum with a second strip blotted from a different prep gel of J5 LPS. Eleven of 17 CF sera versus 3 of 9 convalescent PA bacteremic sera showed core bands below 14 kD (p>0.1, Chi square with the Yates modification). These core bands were in the same location that immunoblotted rabbit anti-J5 LPS appeared on silver stain (FIG. 2, lane B). Hence it was highly unlikely that the difference between CF patients and convalescent PA bacteremic patients in IgG anti-PA core LPS response was simply due to cross-reactive antibodies to the common endotoxic core of enteric gram-negative bacilli.

As may be appreciated from the foregoing, the present invention provides those skilled in the art with novel compositions and methods useful in the diagnosis and monitoring of *P. aeruginosa* infections. Such compositions and methods are provided in kit form for ready use.

Although the present invention has been described in some detail by way of illustration and example for purposes of clarity of understanding, it will be obvious that certain changes and modifications may be practiced within the scope of the appended claims.

What is claimed is:

1. A method for detecting a chronic *Pseudomonas aeruginosa* infection in a donor having cystic fibrosis by screening for an immunoglobulin molecule specific for an antigenic determinant on lipopolysaccharide derived from a *Pseudomonas aeruginosa* strain PAC 605 cell having A.T.C.C. Accession No. 53273, said method comprising the steps of:
   a) collecting serum from said donor;
   b) contacting said serum with said lipopolysaccharide; and
   c) detecting a chronic *Pseudomonas aeruginosa* infection by determining whether the level of said immunoglobulin in said serum is significantly higher than the level of said immunoglobulin in a non-infected or convalescent donor.

2. The method according to claim 1, wherein said donor is a human.

3. The method according to claim 1, wherein said immunoglobulin is of class IgG.

4. The method according to claim 1, wherein said lipopolysaccharide is bound to a support prior to contacting with said serum.

5. A method for the diagnosis of chronic *Pseudomonas aeruginosa* infection in a donor having cystic fibrosis by screening sample serum with lipopolysaccharide derived from a *Pseudomonas aeruginosa* strain PAC 605 cell having A.T.C.C. Accession number 53273, said method comprising steps of:
   a) contacting sample serum from a donor suspected of having cystic fibrosis or chronic *Pseudomonas aeruginosa* with said lipopolysaccharide; and
   b) measuring the IgG titer to said lipopolysaccharide in said sample serum and detecting a chronic *Pseudomonas aeruginosa* infection by determining whether said IgG titer is significantly higher than a base IgG titer in serum from a donor known to be non-infected with *Pseudomonas aeruginosa* or in convalescent serum from a donor recovering from *Pseudomonas aeruginosa* infection.

* * * * *